United States Patent [19]

Hoelderich et al.

[11] Patent Number: 4,990,684
[45] Date of Patent: Feb. 5, 1991

[54] PREPARATION OF PHENYLACETALDEHYDES

[75] Inventors: Wolfgang Hoelderich, Frankenthal; Norbert Goetz, Worms; Leopold Hupfer, Friedelsheim, all of Fed. Rep. of Germany

[73] Assignee: BASF Aktiengesellschaft, Ludwigshafen, Fed. Rep. of Germany

[21] Appl. No.: 378,984

[22] Filed: Jul. 12, 1989

[30] Foreign Application Priority Data

Jul. 21, 1988 [DE] Fed. Rep. of Germany ....... 3824725

[51] Int. Cl.$^5$ ...................... C07C 45/41; C07C 45/51
[52] U.S. Cl. ..................................... 568/435; 568/426
[58] Field of Search ................................ 568/435, 426

[56] References Cited

U.S. PATENT DOCUMENTS 3,925,458 12/1975 Kogure et al. ....................... 568/435
4,585,900 4/1986 Holy et al. ........................... 568/435

FOREIGN PATENT DOCUMENTS 2404158 8/1974 Fed. Rep. of Germany ....... 568/435

Primary Examiner—Werren B. Lone
Attorney, Agent, or Firm—Keil & Weinkauf

[57] ABSTRACT

Phenylacetaldehydes of the general formula I

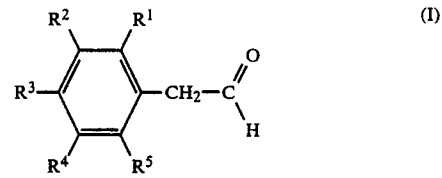

where each of $R^1$ to $R^5$ is independently of the others hydrogen, halogen, unsubstituted or halogen-substituted alkyl, alkenyl, alkoxyl, alkylthio or cycloalkyl, are prepared by converting glycidic esters of the general formula II

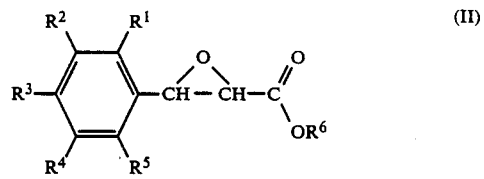

where each of $R^1$ to $R^5$ is as defined above and $R^6$ is tertbutyl or i-propyl, in the presence of zeolites and/or phosphates and/or phosphoric or boric acid on a carrier material and/or acidic metal oxides as catalysts.

10 Claims, No Drawings

PREPARATION OF PHENYLACETALDEHYDES

The present invention relates to a process for preparing phenylacetaldehydes from glycidic esters by simultaneous decarboxylation and deolefination in the presence of zeolites and/or phosphates and/or phosphoric or boric acid on a carrier material and/or acidic metal oxides as catalysts.

Phenylacetaldehydes are useful intermediates for preparing novel active substances for insecticides, fungicides, herbicides and drugs.

Known methods for preparing phenylacetaldehydes, which can also be practised on an industrial scale, are:

The dehydrogenation of phenylethanols leads only to partial conversions, entailing the wasteful separation of starting material and end product (phenylacetaldehydes are thermolabile), and the formation of self-condensation products in the course of fractionation. The preparation of halogen-containing phenylacetaldehydes is not possible in this way since dehalogenation takes place under the reaction conditions.

The rearrangement of styrene oxides likewise leads in general only to partial conversions, difficult-to-remove by-products, poor selectivities and short catalyst lives, owing to surface deposits.

It is also known that phenylacetaldehydes can be obtained by rearrangement of styrene glycol over an aluminum silicate with $SiO_2:Al_2O_3=80:20$ 93:7 mixed with for example iron oxide, calcium oxide or magnesium oxide or over activated clay in suspension under reduced pressure. These two methods have in common that the yields at from 50 to 86 % are still in need of improvement. Similarly, this method is not flexible, since no halogenated compounds are obtained. Moreover, clay is a natural mineral which, depending on provenience, has different compositions and hence different catalytic properties, and selectivities. This is an obstacle in particular to use in a continuous industrial process.

Aldehydes are also obtainable from carbonyl chlorides by a Rosenmund reduction. Such reactions proceed smoothly in the liquid phase with acryloyl chlorides. Other acyl chlorides, for example aralkylcarbonyl chlorides, generally give lower yields coupled with catalyst poisoning.

We have found a process for preparing a phenylacetaldehyde of the general formula I

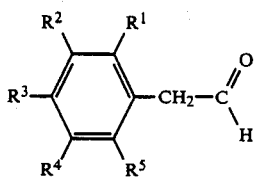

where each of $R^1$ to $R^3$ is independently of the others hydrogen, halogen, unsubstituted or halogen-substituted alkyl, alkenyl, alkoxyl, alkylthio or cycloalkyl, by converting a glycidic ester of the general formula II

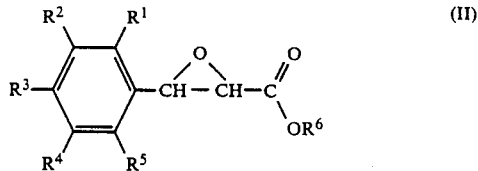

where each of $R^1$ to $R^5$ is as defined above and $R^6$ is tertbutyl or i-propyl, in the presence of a zeolite or a phosphate or phosphoric or boric acid on a carrier material or an acidic metal oxide as a catalyst with simultaneous decarboxylation and deolefination.

The process according to the invention remedies the abovementioned disadvantages of existing processes.

The present invention makes it possible to prepare phenylacetaldehydes I from readily accessible starting materials in the presence of catalysts which are notable for simple availability, high activity and easy regenerability. Furthermore, long catalyst lifetimes are obtained together with high conversions, high selectivities and catalyst flexibility in respect of the starting materials.

The advantages of the novel process carried out over the novel catalysts are: complete conversion, absence of separating problems, long lifetimes, selectivities >90 %, very good yields even with halogencontaining starting materials, simple isolation of the end products, reuse in general without additional purification, and easy regenerability of the catalysts in the event of coking.

Each of $R^1$ to $R^5$, which can be identical to or different from the others, is for example methyl, ethyl, n-/i-propyl, n-/i-/t-butyl, hexyl, octyl, decyl, dodecyl, cyclopentyl, cyclohexyl, trifluoromethyl, trichloromethyl, trifluoromethoxy, fluoromethyl, chloromethyl, fluorocyclopentyl, ethenyl, propenyl, butenyl, hexenyl, octenyl, decenyl, dodecenyl, cyclopentenyl, cyclohexenyl, fluorocyclopentenyl, trifluoromethylthio, fluorine and chlorine.

$R^6$ is tert-butyl or i-propyl.

The catalysts used for the process according to the invention are acidic zeolitic catalysts. Zeolites are crystalline aluminosilicates which possess a highly ordered structure comprising a rigid three-dimensional network of $SiO_4$ and $AlO_4$ tetrahedra joined together by common oxygen atoms. The ratio of the Si and Al atoms oxygen is 1:2 (see Ullmanns Encyclopdie d. techn. Chemie, 4th edn., vol. 24, p. 575 (1983)). The electrovalence of the aluminum-containing tetrahedra is balanced by the inclusion in the crystal of cations, for example an alkali metal or hydrogen ion. Cation exchange is possible. The spaces between the tetrahedra are occupied prior to dehydration by drying or calcination by water molecules.

In zeolites, the aluminum in the lattice may also be replaced by other elements such as B, Ga, Fe, Cr, V, As, Sb, Bi or Be or mixtures thereof, or the silicon may be replaced by a tetravalent element such as Ge, Ti, Zr or Hf.

According to structure, zeolites are subdivided into various groups (see Ullmanns Encyclopädie d. techn. Chemie, 4th edn., vol. 24, p. 575 (1983)). For instance, in the mordenite group the zeolite structure is formed by chains and in the chabazite group it is formed by layers of tetrahedra, while in the faujasite group the tetrahedra are arranged into polyhedra, for example in the form of a cuboctahedron composed of four- or sixmembered rings. Depending on the link between the cuboctahedra, from which differently sized voids and pores arise, zeolites are classified as of Type A, L, X or Y.

Suitable catalysts for the process according to the invention are zeolites of the mordenite group or narrow-pored zeolites of the erionite or chabazite type or zeolites of the faujasite type, for example Y-, X- or L-zeolites. This group of zeolites also includes the ultrastable zeolites of the faujasite type, ie. dealuminized zeolites. Processes for preparing such zeolites are described in Catalysis by Zeolites, volume 5 of Studies in Surface Science and Catalysis, ed. B. Imelik et al., Elsevier Scientific Publishing Comp., 1980, page 203, and Crystal Structures of Ultra-stable Faujasites, Advances in Chemistry Series No. 101, American Chemical Society Washington DC, pages 226 et seq. (1971), and in U.S. Pat. No. 4,512,961.

It is particularly advantageous to use zeolites of the pentasil type. Their common building block is a five-membered ring composed of $SiO_4$ tetrahedra. They are characterized by a high $SiO_4/Al_2O_3$ ratio and by pore sizes between those of the zeolites of Type A and those of Type X or Y (cf. Ullmanns Encyclopdie d. techn. Chem., 4th edn., vol. 24, 1983).

These zeolites may have different chemical compositions.. They are aluminosilicate, borosilicate, iron silicate, beryllium silicate, gallium silicate, chromium silicate, arsenic silicate, antimony silicate and bismuth silicate zeolites or mixtures thereof and aluminogermanate, borogermanate, gallium germanate and iron germanate zeolites or mixtures thereof. Specifically, aluminosilicate, borosilicate and iron silicate zeolites of the pentasil type are suitable for the process according to the invention. The aluminosilicate zeolite is prepared for example from an aluminum compound, preferably $Al(OH)_3$ or $Al_2(SO_4)_3$, and from a silicon component, preferably finely divided silicon dioxide, in an aqueous amine solution, in particular in polyamines such as 1,6-hexanediamine or 1,3-propanediamine or triethylenetetramine solution, with or in particular without the addition of alkali metal or alkaline earth metal at from 100 to 220° C. under autogenous pressure. This also includes the isotactic zeolites described in EP-A-34,727 and EP-A-46,504. The aluminosilicate zeolites obtained have an $SiO_2/Al_2O_3$ ratio of from 10 to 40,000, depending on the choice of starting quantities. It is also possible to synthesize such aluminosilicate zeolites in an ethereal medium, such as diethylene glycol dimethyl ether, in an alcoholic medium such as methanol or 1,4-butanediol, or in water.

The borosilicate zeolite is synthesized for example at from 90 to 200° C. under autogenous pressure by reacting a boron compound, for example $H_2BO_3$, with a silicon compound, preferably finely divided silicon dioxide, in an aqueous amine solution, in particular in 1,6-hexanediamine or 1,3-propanediamine or triethylenetetramine solution, with or in particular without the addition of an alkali metal or alkaline earth metal. Isotactic zeolites as described in EP-A-34,727 and EP-A-46,504 are also suitable. These borosilicate zeolites can also be prepared by carrying out the reaction not in an aqueous amine solution but in an ethereal solution, for example in diethylene glycol dimethyl ether, or in an alcoholic solution,.for example 1,6-hexanediol, The iron silicate zeolite is obtained for example from an iron compound, preferably $Fe_2(SO_4)_3$, and a silicon compound, preferably finely divided silicon dioxide, in an aqueous amine solution, in particular 1,6-hexanediamine, with or without the addition of an alkali metal or alkaline earth metal, at from 100 to 220° C. under autogenous pressure.

The usable high-silicon zeolites ($SiO_2/Al_2O_3 \geq 10$) also include the ZSM types, ferrierite, Nu-1 and Silicalit ®, a molecular sieve and a silica polymorph.

The aluminosilicate, borosilicate and iron silicate zeolites thus prepared, after they have been isolated, dried at from 100 to 160° C, preferably at 110° C, and calcined at from 450 to 550° C, preferably at 500° C., can be molded with a binder in a ratio of from 90:10 to 0:60 % by weight into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided $Al_2O_3$, $TiO_2$, $ZrO_2$ and clay. After molding, the extrudates or pellets are dried at 110° C. over 16 h and calcined at 500° C. over 16 h.

Advantageous catalysts are also obtained on molding the isolated aluminosilicate or borosilicate zeolite directly after drying and subjecting it to a calcination only after molding. The synthesized aluminosilicate and borosilicate zeolites can be used in the pure form, without binder, as extrudates or tablets, in which case the extruding or peptizing aids used are for example ethylcellulose, stearic acid, potato starch, formic acid, oxalic acid, acetic acid, nitric acid, ammonia, amines, silicoesters and graphite or mixtures thereof.

If the zeolite, owing to its manner of preparation, is present not in the catalytically active, acidic H-form but for example in the Na-form, it can be completely or partially converted into the desired H-form by ion exchange, for example with ammonium ions, and subsequent calcination or by treatment with acids.

If in the course of the use according to the invention of the zeolitic catalysts deactivation occurs due to the deposition of coke, it is advisable to regenerate the zeolites by burning off the coke deposit with air or with an air/Nz mixture at from 400 to 550° C, preferably at 500° C. This restores the zeolites to their initial activity.

By partial precoking it is possible to set the activity of the catalyst for optimum selectivity in respect of the desired reaction product.

To obtain maximum selectivity, high conversion and long catalyst lives, it may be advantageous to modify the zeolites. A suitable modification of the catalyst comprises for example doping the unmolded or molded zeolites with metal salts by ion exchange or impregnation. The metals used are alkali metals such as Li, Cs or K, alkaline earth metals such as Mg, Ca or Sr, metals of main groups 3, 4 and 5 such as Al, Ga, Ge, Sn, Pb or Bi, transition metals of subgroups 4 to 8 such as Ti, Zr, V, Nb, Cr, Mo, W, Mn, Re, Fe, Ru, Os, Co, Rh, Sr, Ni, Pd or Pt, transition metals of subgroups 1 and 2 such as Cu, Ag or Zn, or rare earth metals such as La, Ce, Pr, Nd, Fr, Yb or U.

Advantageously, the doping is carried out, for example, by introducing the molded zeolites initially in a riser tube and, for example, passing an aqueous or ammoniacal solution of a halide or a nitrate of the metals described over it at from 20 to 100° C. Such an ion exchange can be effected for example, on the hydrogen, ammonium and alkali metal form of the zeolite. A further way of applying metal to the zeolite comprises impregnating the zeolitic material, for example with a halide, a nitrate or an oxide of the metals described in aqueous, alcoholic or ammoniacal solution. Not only ion exchange but also impregnation are followed by at least one drying operation, alternatively by a further calcination.

A possible embodiment comprises, for example, dissolving Cu(NO$_3$($_2$X3H$_2$O or Ni(NO$_3$)$_2$X6H$_2$O or Ce(NO$_3$)$_3$X6H$_2$O or La(NO$_3$)$_2$X6H$_2$O or Cs$_2$CO$_3$ in water. The molded or unmolded zeolite is impregnated with this solution for a certain time, say 30 minutes. Any supernatant solution is stripped of water in a rotary evaporator. Thereafter the impregnated zeolite is dried at about 150° C. and calcined at about 550° C. This impregnation can be carried out repeatedly in succession in order to obtain the desired metal content.

It is also possible to prepare, for example, an aqueous Ni(CO$_3$)$_2$ solution or ammoniacal Pd(NO$_3$)$_2$ solution and to suspend the pure pulverulent zeolites therein at from 40 to 100° C. by stirring for about 24 hours. Following filtration, drying at about 150° C. and calcination at about 500° C., the zeolitic material thus isolated can be further processed with or without binders into extrudates, pellets or fluidizable material.

An ion exchange on the zeolites present in the H-form or ammonium form or alkali metal form can be effected by introducing the zeolites initially in extrudates or pellets into a column and passing, for example, an aqueous Ni(NO$_3$)$_2$ solution or ammoniacal Pd(NO$_3$)$_2$ solution at a slightly elevated temperature of from 30 to 80° C. over it in a cycle for from 15 to 20 hours. This is followed by washing with water, drying at about 150° C. and calcining at about 550° C. With some metal-doped zeolites such as the Pd-, Cu- or Ni-doped zeolites, an aftertreatment with hydrogen is advantageous.

A further modifying technique comprises subjecting the zeolitic material, molded or unmolded, to a treatment with acids such as hydrochloric acid, hydrofluoric acid and phosphoric acid and/or steam. For example, and advantageous procedure is to treat zeolites in powder form with 1 N phosphoric acid at 80° C for 1 hour, washing with water, drying at 110° C over 16 hours and calcining at 500° C. over 20 hours. In another procedure, zeolites are treated before or after molding with binders with from 3 to 25 % strength by weight, in particular from 12 to 20 % strength by weight, aqueous hydrochloric acid at from 60 to 80° C, for example from 1 to 3 hours. Thereafter the zeolite thus treated is washed with water, dried and calcined at from 400 to 500° C.

A particular form of the acid treatment comprises treating the zeolitic material before it is molded with in general from 0.001 N to 2 N, preferably from 0.05 N to 0.5 N, hydrofluoric acid for from in general 0.5 to 5, preferably from 1 to 3, hours at an elevated temperature, for example by refluxing. After the zeolitic material is isolated for example by filtration and washing, it is advantageously dried, for example at from 100 to 160° C, and calcined at in general from 450 to 600° C. In another preferred form of the acid treatment, the zeolitic material, after molding with binder, is treated at elevated temperatures, advantageously at from 50 to 90° C., preferably at from 60 to 80° C, preferably with from 12 to 20 % strength by weight hydrochloric acid for from 0.5 to 5 hours. Thereafter the zeolitic material is in general washed and advantageously dried, for example at from 100 to 160° C., and calcined at in general from 450 to 600° C. An HF treatment may also be followed by an HCl treatment.

In another procedure, zeolites can be modified by applying phosphorus compounds, such as trimethoxyphosphate, trimethoxyphosphine or primary, secondary or tertiary sodium phosphate. The treatment with primary sodium phosphate has proved particularly advantageous. Here the zeolites are impregnated in extruded, tablet or fluidized form with aqueous NaHPO. solution, dried at 110° C. and calcined at 500° C.

Further catalysts for the process according to the invention are phosphates, in particular aluminum phosphates, silicon aluminum phosphates, silicon iron aluminum phosphates, cerium phosphate, zirconium phosphates, boron phosphate, iron phosphate and mixtures thereof.

Aluminum phosphate catalysts used for the process according to the invention are in particular hydrothermally synthesized aluminum phosphates which possess the zeolite structure.

Hydrothermally synthesized aluminum phosphates are for example APO-5, APO-9, APO-11, APO-12, APO-14, APO-21, APO-25, APO-31 and APO-33. Syntheses of these compounds are described in EP 132,708, U.S. Pat. No. 4,310,440 and U.S. Pat. No. 4,473,663.

AlPO$_4$-5 (APO-5) for example is synthesized by homogeneously mixing orthophosphoric acid with pseudoboehmite (Catapal SB®) in water, adding tetrapropylammonium hydroxide, and then reacting in an autoclave at about 150° C. under autogenous pressure for from 20 to 60 hours. The AlPO is filtered off, dried at from 100 to 160° C. and calcined at from 450 to 550° C.

AlPO$_4$-9 (APO-9) is likewise synthesized from orthophosphoric acid and pseudoboehmite but in aqueous DABCO solution (1,4-diazabicyclo[2.2.2]octane) at about 200° C. under autogenous pressure in the course of from 200 to 400 hours.

AlPO$_4$-21 (APO-21) is synthesized from orthophosphoric acid and pseudoboehmite in aqueous pyrrolidone solution at from 150 to 200° C. under autogenous pressure in the course of from 50 to 200 hours.

The silicon aluminum phosphates used for the process according to the invention are for example SAPO5, SAPO-11, SAPO-31 and SAPO-34. The synthesis of this compound is described, for example, in EP 103,117 and U.S. Pat. No. 4,440,871 SAPOs are prepared by crystallization from aqueous mixture at from 100 to 250° C. under autogenous pressure in the course of from 2 hours to 2 weeks, during which the reaction mixture comprising a silicon component, an aluminum component and a phosphorus component is converted in aqueous organoamine solutions.

SAPO-5, for example, is obtained by mixing SiO$_2$ suspended in aqueous tetrapropylammonium hydroxide solution with an aqueous suspension of pseudoboehmite and orthophosphoric acid and subsequent reaction at 150–200° C. for from 20 to 200 hours under autogenous pressure in a stirred autoclave. The powder is filtered off, dried at from 110 to 160° C. and calcined at from 450 to 550° C.

Phosphorus catalysts used for the process also include precipitated aluminum phosphates. Such aluminum phosphate is prepared for example by dissolving 92 g of diammonium hydrogenphosphate in 700 ml of water. 260 g of Al(NO$_3$)$_3$xH$_2$O in 700 ml of water are added dropwise over 2 hours, during which the pH is maintained at pH 8 by the simultaneous addition of 25 % strength NH$_3$ solution. The resulting precipitate is subsequently stirred for 12 hours, and then filtered off with suction and washed. It is dried at 60° C. over 16 h.

Boron phosphates for the process according to the invention can be prepared for example by mixing and kneading concentrated boric acid and phosphoric acid and subsequent drying and calcination in an inert gas, air or steam atmosphere at from 250 to 650° C., preferably at from 300 to 550° C.

These phosphates can have applied to them, by impregnation (soaking and spraying), or in some cases even by ion exchange, modifying components of the type described above for zeolites. Here too it is possible, as with the zeolite catalysts, for a modification with acids to take place.

Suitable acidic catalysts also include for example the acidic oxides of elements of main groups III and IV and subgroups IV to VI of the periodic table, in particular oxides such as silicon dioxide in the form of silica gel, kieselguhr, quartz, also titanium dioxide, zirconium dioxide, phosphorus oxides, vanadium oxides, niobium oxides, boron oxides, chromium oxides, molybdenum oxides, tungsten oxides or pumice or mixtures thereof. These oxides can likewise be doped by the application of modifying components of the type described above for zeolite catalysts. The treatment with acids as described above for zeolite catalysts is likewise a possible method of modification.

It is also possible to use catalysts impregnated with phosphoric acid or boric acid. Phosphoric acid or boric acid is applied to an $SiO_2$, $Al_2O_3$ or pumice carrier material, for example by impregnating or spraying. A catalyst which contains phosphoric acid can be obtained for example by impregnating $SiO_2$ with $H_3PO_4$, $NaH_2PO_4$ or $Na_2HPO_4$ solution and subsequent drying or calcination. However, phosphoric acid can also be sprayed together with silica gel in a spray tower; this is followed by a drying step and usually by a calcination. Phosphoric acid can also be sprayed onto the carrier material in an impregnating mill.

The catalysts described here can be optionally used as from 2 to 4 mm extrudates or as tablets from 3 to 5 mm in diameter or as chips from 0.1 to 0.5 mm in particle size or in fluidizable form.

The reaction conditions generally chosen for the conversion according to the invention in the preferred gas phase are 100–500° C., preferably 200–350 C., and a weight hourly space velocity (WHSV) of from 0.1 to 20 $h^{-1}$, preferably from 0.5 to 5 $h^{-1}$(of g of starting mixture per g of catalyst per hour). The reaction can be carried out in a fixed bed or alternatively a fluidized bed.

It is also possible to carry out the reaction in the liquid phase (either a suspension, trickle bed or liquid phase procedure) at from 50 to 200° C.

The process is in general carried out under atmospheric pressure or, depending on the volatility of the starting compound, under reduced or superatmospheric pressure, possibly batchwise but preferably continuously.

Sparingly volatile or solid starting materials are used in a dissolved form, for example in THF, toluene or petroleum ether solution. In general, dilution of the starting material with such solvents or with inert gases such as $N_2$, Ar or $H_2O$ vapor is possible.

After the reaction has ended, the resulting products are isolated from the reaction mixture in a conventional manner, for example by distillation; unconverted starting mixture is recycled if necessary for conversion according to the invention.

The following Examples illustrate the invention:

The catalysts used for the process according to the invention are:

CATALYST A

The borosilicate zeolite of the pentasil type is prepared in a hydrothermal synthesis from 640 g of finely divided $SiO_2$, 122 g of $H_3BO_3$ and 8000 g of an aqueous 1,6-hexanediamine solution (mixture 50:50 % by weight) at 170° C under autogenous pressure in a stirred autoclave. After filtration and washing, the crystalline reaction product is dried at 100° C. over 24 h and calcined at 500° C. over 24 h. This borosilicate zeolite is composed of 94.2 % by weight of SiO: and 2.3 % by weight of $B_2O_3$.

This material is used to produce by molding with a molding aid 2 mm extrudates which are dried at 110° C. over 16 h and calcined at 500° C. over 24 h.

CATALYST B

An aluminosilicate zeolite of the pentasil type was prepared under hydrothermal conditions under autogenous pressure and at 150° C. from 65 g of finely divided $SiO_2$ and 20.3 g of $Al_2(SO_4)_3 \times 18H_2O$ in 1 kg of an aqueous 1,6hexanediamine solution (mixture 50:50 % by weight) in a stirred autoclave. The crystalline reaction product was filtered off, washed, dried at 110° C. over 24 h and calcined at 500° C. over 24 h. This aluminosilicate zeolite contained 91.6 % by weight of $SiO_2$ and 4.6 % by weight of $Al_2O_3$.

The catalyst was molded with a molding aid into 2 mm extrudates, dried at 110° C. over 16 h and calcined at 500° C. over 24 h.

CATALYST C

Catalyst C is obtained by impregnating the extrudates of Catalyst A with an aqueous $Cs_2CO_3$ solution, then drying at 130° C. over 2 h and calcining at 540° C. over 2 h. The Cs content is 0.6 % by weight.

CATALYST D

The iron silicate zeolite of the pentasil type was synthesized under hydrothermal conditions at autogenous pressure and 165° C. from 273 g of sodium silicate, dissolved in 253 g of an aqueous 1,6-hexanediamine solution (mixture 50:50 % by weight), and 31 g of iron sulfate, dissolved in 21 g of 96 % strength sulfuric acid and 425 g of water, in a stirred autoclave over 4 days. The zeolite was filtered off, washed, dried at 100° C. over 24 hours and calcined at 500° C. over 24 hours. The result obtained was an iron silicate zeolite having an $SiO_2/Fe_2O_3$ ratio of 17.7 and an $Na_2O$ content of 1.2 % by weight. The catalyst was extruded together with finely divided $SiO_2$ in a weight ratio of 70:30 into 2.5-mm extrudates, which were dried at 110° C. over 16 hours and calcined at 500° C. over 24 hours. These extrudates are ion exchanged with 20 % strength NH Cl solution at 80° C. and then washed until chloride-free, dried at 110° C. and calcined at 500° C. over 5 hours. The ion exchange is continued until the Na content is 0.002 % by weight.

CATALYST E

Catalyst E is prepared in the same way as catalyst C, except that $Cs_2CO_3$ is replaced by $Ce(NO_3)_2$. The Ce content is 1.8 % by weight.

CATALYST F

Silicon aluminum phosphate-5 (SAPO-5) is prepared from a mixture of 200 g of 98 % strength phosphoric acid, 136 g of boehmite, 60 g of silica gel 130 % strength), 287 g of tripropylamine and 587 g of H₂O. This mixture is reacted at 150° C. under autogenous pressure for 168 hours. The crystalline product is filtered off, dried at 120° C. and calcined at 500° C. SAPO-5 contains 49.8 % by weight of P₂O₅, 33.0% by weight of Al₂O₃ and 6.2 % by weight of SiO₂. SAPO-5 is molded with an extrusion aid into 3 mm extrudates, dried at 120° C. and calcined at 500° C.

CATALYST G

Commercial zirconium phosphate Zr₃(PO₄)₄ is molded in pure form.

CATALYST H

BPO₄ is prepared by adding 49 g of H₃BO₃ together with 117 g of H₃PO₄ (75 % strength) in a kneader, evaporating off excess water and molding the reaction product into 3-mm extrudates. These extrudates are dried at 100° C. and calcined at 350° C. Catalyst H contains 8.77 % by weight of B and 28.3 % by weight of P.

CATALYST I

TiO₂ P 25 ® is molded into 2-mm extrudates, which are dried at 110° C and calcined at 500° C. over 16 hours.

CATALYST J

D 10-10 ® Al₂O₃ is impregnated with H₂BO₃, dried at 110° C. and calcined at 500° C. over 5 hours. Catalyst J is composed of 85 % of Al₂O₃ and 15 % of B₂O₃.

The experimental conditions and results obtained with these catalysts are given in Tables 1 and 2.

EXAMPLES 1 TO 15

The reactions were carried out in the gas phase under isothermal conditions in a tubular reactor (coil, 0.6 cm internal diameter, 90 cm length) for not less than 6 hours. The reaction products were separated off and characterized in a conventional manner. The reaction products and starting materials were quantitatively determined by gas chromatography.

The results are given in Tables 1 and 2.

EXAMPLE 16

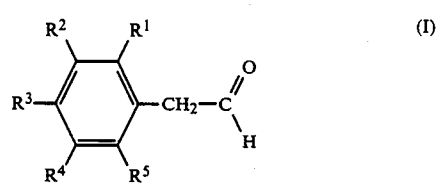

100 g of tert-butyl p-tert-butylphenylglycidate are passed per hour in cocurrent with 400 standard liters of nitrogen per hour over a hot boron zeolite catalyst A at 260° C. located in an electrically heated 1 liter tubular reactor. The reaction products leaving the reactor are condensed and worked up by distillation. This gives p-tert-butylphenylacetaldehyde (bp. =87° C./ 0.4 mbar) in a yield of 92% of theory.

We claim:

1. A process for preparing a phenylacetaldehyde of the formula I

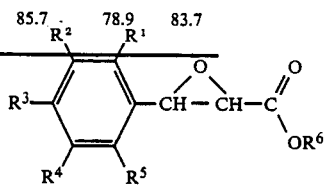

where each of $R^1$ to $R^2$ is independently of the others hydrogen, halogen, unsubstituted or halogen-substituted alkyl, alkenyl, alkoxyl, alkylthio or cycloalkyl, which comprises heating a glycidic ester of the formula II (II)

TABLE 1

| Conversion of tert-butyl p-methylphenylglycidate into p-methylphenylacetaldehyde |
| --- |

| Example | 1 | 2 | 3 | 4 | 5 | 6 | 7 | 8 | 9 | 10 | 11 |
| --- | --- | --- | --- | --- | --- | --- | --- | --- | --- | --- | --- |
| Catalyst | A | A | B | C | D | E | F | G | H | I | J |
| Temp., °C. | 350 | 300 | 250 | 250 | 250 | 250 | 300 | 250 | 250 | 300 | 300 |
| WHSV h⁻¹ | 3 | 3 | 3 | 3 | 3 | 3 | 3 | 3 | 3 | 3 | 3 |
| Conversion % | 100 | 100 | 100 | 100 | 100 | 100 | 100 | 100 | 100 | 100 | 100 |
| Selectivity % | 93.5 | 89.2 | 87.2 | 94.0 | 87.9 | 89.9 | 87.1 | 80.1 | 85.7 | 78.9 | 83.7 |

TABLE 2

| Conversion of substituted tert-butyl phenylglycidates into the corresponding phenylacetaldehydes |
| --- |

| Example | 12 | 13 | 14 | 15 |
| --- | --- | --- | --- | --- |
| Substituent | p-fluoro | p-methoxy | p-trifluoro-methyl | 1-methyl-4-fluoro |
| Catalyst | A | A | A | A |
| Temperature °C. | 250 | 250 | 250 | 250 |
| WHSV⁻¹ | 3 | 3 | 3 | 3 |
| Conversion % | 100 | 100 | 100 | 100 |
| Selectivity % | 91.9 | 90.1 | 93.9 | 88.7 | where each of $R^1$ to $R^5$ is as defined above and $R^6$ is tert-butyl or i-propyl, in a gas phase or liquid-phase conversion of II to I in the presence of a zeolite or a phosphate or phosphoric or boric acid on a carrier material or an acidic metal oxide as a catalyst, the temperature in the gas-phase being from 100 to 500° C. and the temperature in the liquid-phase being from 50 to 200° C.

2. A process as defined in claim 1, wherein the catalyst used is a zeolite of the pentasil type.

3. A process as defined in claim 1, wherein the catalyst used is an aluminosilicate zeolite, a borosilicate zeolite or an iron silicate zeolite of the pentasil type.

4. A process as defined in claim 1, wherein the catalyst used is a zeolite of the faujasite type.

5. A process as defined in claim 1, wherein the catalyst used is a zeolite doped with an alkali metal, a transition metal or a rare earth metal.

6. A process as defined in claim 1, wherein the catalyst used is a phosphate or one of the elements B, Al, Zr, Ce, Fe and Sr or a mixture of such phosphates, or a hydrothermally synthesized phosphate.

7. A process as defined in claim 1, wherein the catalyst used is a hydrothermally synthesized aluminum phosphate or silicon aluminum phosphate or silicon iron aluminum phosphate or boron aluminum phosphate.

8. A process as claimed in claim 1, wherein the catalyst used is phosphoric acid or boric acid on an $SiO_2$, $Al_2O_3$, $TiO_2$ or pumice carrier material.

9. A process as defined in claim 1, wherein the catalyst used is an acidic oxide of one of the metals Ti, Zr, Al, Si, V, W, Nb and Cr.

10. A process as defined in claim 1, wherein the reaction is carried out in the gas phase.

* * * * *